United States Patent [19]

Griffith

[11] Patent Number: 5,171,885
[45] Date of Patent: Dec. 15, 1992

[54] L-BUTHIONINE-S-SULFOXIMINE AND L-BUTHIONINE-R-SULFOXIMINE

[75] Inventor: Owen W. Griffith, New York, N.Y.

[73] Assignee: Cornell Research Foundation, Inc., Ithaca, N.Y.

[21] Appl. No.: 715,898

[22] Filed: Jun. 19, 1991

Related U.S. Application Data

[63] Continuation of Ser. No. 359,886, Jun. 1, 1989, abandoned.

[51] Int. Cl.$^5$ ............................................. C07C 53/128
[52] U.S. Cl. ....................................... 562/556; 562/554
[58] Field of Search ......................... 562/556, 554, 557

[56] References Cited

PUBLICATIONS

Bump, E. A., et al, Int. J. Radiation Oncology Biol., Phys., vol. 8, 439–442 (1982).
Ozols, R. F., et al, Biochemical Pharmacology, vol. 36, No. 1, 147–153 (1987).
Kramer, R. A., et al, Int. J. Radiation Oncology Biol. Phys., vol. 16, 1325–1329 (May 1989).
McNally, N. J., et al, Int. J. Radiation Oncology Biol. Phys., vol. 16, 1331–1334 (May 1989).
Arrick, B. A., et al, J. Exp. Med, vol. 153, 720–725 (Mar. 1981).
Brodie, A. E., et al, Toxicology and Applied Pharmacology, 77, 381–387, 1985.
Anderson, M. E., et al, Proc. Natl. Acad. Sci. USA, vol. 80, pp. 707–711, Feb. 1983.
Richman, Paul G., et al, The Journal of Biological Chemistry, 248, No. 19, 6684–6690, 1973.
Griffith, O. W., Anal. Biochem. 106, 207–212 (1980).
Glutathione Centennial Molecular Perspectives and Clinical Implications (Taniguchi, N., et al, eds.), 1989, Academic Press, pp. 285–299. (Chapter titled "L-Buthionine–SR–Sulfoximine: Mechanism of Action, Resolution of Diastereomers and Use as a Chemotherapeutic Agent," by Owen W. Griffith.
Christensen, B. W., et al, Chemical Communications, pp. 169–170 (1969).
Griffith, W. W., The Journal of Biological Chemistry, vol. 257, No. 22, pp. 13704–13712 (1982).

*Primary Examiner*—Marianne M. Cintins
*Assistant Examiner*—Margaret Argo

[57] ABSTRACT

The pure isomers L-buthionine-S-sulfoximine and L-buthionine-R-sulfoximine are provided. The L-S-isomer has utility, for example, in causing the depletion of glutathione, a major protectant molecule in tumors and certain parasites. The L-R-isomer has utility as a compound decreasing further uptake and thus effect of the L-S-isomer and for causing glutathione depletion specific to the kidney. The isolation of pure isomers from L-buthionine-SR-sulfoximine enables treatment at lower dosages without cross effects.

The pure L-buthionine-S-sulfoximine isomer is obtained from L-buthionine-SR-sulfoximine by recrystallization preferably by forming a solution of L-buthionine-SR-sulfoximine in water at a concentration of 0.8M and cooling to form crystals enriched in the L-R-isomer and a filtrate enriched in L-S-isomer, drying the filtrate to obtain a solid, dissolving the solid in ethanol, adding trifluoroacetic acid to form acid salt and provide solvent, then adding hexane to cause crystal formation, then converting the crystals to the free zwitterion using ion exchange resin.

Both isomers can be separated concurrently by reverse phase chromatography in Cu$^{++}$/D-proline buffers.

5 Claims, No Drawings

L-BUTHIONINE-S-SULFOXIMINE AND L-BUTHIONINE-R-SULFOXIMINE

This invention was made at least in part with Government support under National Institutes of Health grant number DK 26912. The Government has certain rights in the invention.

This is application is a continuation of application Ser. No. 359,886 filed Jun. 1, 1989 now abandoned.

TECHNICAL FIELD

This invention relates to separating the known glutathione biosynthesis inhibitor L-buthionine-SR-sulfoximine into its pure diastereoisomers.

BACKGROUND OF THE INVENTION

Glutathione (gamma-L-glutamyl-L-cysteinylglycine) is synthesized by the sequential action of the enzymes gamma-glutamylcysteine synthetase and glutathione synthetase. L-Buthionine-SR-sulfoximine (L-(S-n-butyl)homocysteine-SR-sulfoximine is a potent and specific inhibitor of gamma-glutamylcysteine synthetase. Glutathione synthesis is decreased in tissues and cells treated in vitro or in vivo with the inhibitor and such cells and tissues become glutathione depleted. Tumors in mice treated with the inhibitor become glutathione depleted and more susceptible to the cytotoxic effects of ionizing radiation and various chemotherapeutic agents. (Bump, E. A., et al, International Journal Radiation Oncology, Biology and Physics, Vol. 8, p. 439–442, 1982 and Ozols, R. F., et al, Biochemical Pharmacology, Vol. 36, No. 1, pp. 147–153, 1987). Moreover, mice infected with *Trypanosoma b. brucei* have been shown to have extended survival and in some cases to be cured by treatment with DL-buthionine-SR-sulfoximine. (Arrick, B. A., et al, J. Exp. Med, Vol. 153, 720–725, March 1981).

A problem encountered in utilizing either DL-buthionine-SR-sulfoximine or L-buthionine-SR-sulfoximine is that very large dosages are often required and such dosages become osmotically burdensome to the treated subject. It has also been reported that L-buthionine-SR-sulfoximine has a deleterious effect on cystine transport (see Brodie, A. E., et al, Toxicology and Applied Pharmacology 77, 381–387, 1985) and on gamma-glutamylamino acid transport (see Anderson, M. E. and Meister, A., Proc. Natl. Acad. Sci., Vol. 80, pp. 707–711, 1983).

Since it has been shown that L-methionine-S-sulfoximine is the only diastereomer of DL-methionine-SR-sulfoximine that inhibits gamma-glutamylcysteine synthetase (Richman, Paul G., et al, The Journal of Biological Chemistry 248, No. 19, 6684–6690, 1973), it has been suspected that L-buthionine-S-sulfoximine is the only diastereomer of DL-buthionine-SR-sulfoximine that inhibits gamma-glutamylcysteine synthetase. If this were true, then the high dosage and osmotic burden associated with the use of the currently available isomer mixtures could be reduced if the pure L-S-isomer were available. Furthermore, the aforementioned deleterious effect on cystine and gamma-glutamylamino acid transport could be reduced if the pure L-S-isomer were available.

SUMMARY OF THE INVENTION

It has now been discovered how to separate L-buthionine-SR-sulfoximine into its two pure diastereomers, L-buthionine-S-sulfoximine and L-buthionine-R-sulfoximine. It has further been discovered that L-buthionine-S-sulfoximine strongly and irreversibly inhibits gamma-glutamylcysteine synthetase whereas L-buthionine-R-sulfoximine and D-buthionine-SR-sulfoximine are weak and reversible inhibitors of said synthetase. It has also been discovered that in a mouse, administration of L-buthionine-S-sulfoximine depletes tissue glutathione levels in several tissues as effectively as L-buthionine-SR-sulfoximine given at twice the dose. It has further been discovered that L-buthionine-R-sulfoximine has no significant effect on glutathione levels in liver, pancreas and brain and has only a small effect on glutathione level in kidney. Such small effect in the kidney suggests that L-buthionine-R-sulfoximine inhibits gamma-glutamylamino acid transport in the kidney, i.e., has specific action in the kidney.

Thus the invention herein in one embodiment is directed at pure L-buthionine-S-sulfoximine and acid addition salts thereof.

In another embodiment the invention herein is directed at pure L-buthionine-R-sulfoximine and acid addition salts thereof.

In a further embodiment, it has been discovered that pure L-buthionine-S-sulfoximine acid addition salt or pure L-buthionine-S-sulfoximine can be prepared from L-buthionine-SR-sulfoximine by a recrystallization process.

The method for preparing substantially pure L-buthionine-S-sulfoximine acid addition salt or pure L-buthionine-S-sulfoximide from L-buthionine-SR-sulfoximine by recrystallization comprises the steps of:

(a) forming an aqueous solution of L-buthionine-SR-sulfoximine having a concentration ranging from 0.4M to 1.2M and cooling to form crystals enriched in L-buthionine-R-sulfoximine compared to the SR-diastereomeric mixture used and a filtrate enriched in L-buthionine-S-sulfoximine compared to the SR-diastereomeric mixture used, (b) treating the filtrate to produce a substantially water-free solution of L-buthionine sulfoximine enriched in L-buthionine-S-sulfoximine compared to the isomeric ratio in the solution of step (a), in acid-alcohol mixture wherein the acid has a pKa less than 2.0 and then adding a non-polar solvent to produce crystals enriched in L-buthionine-S-sulfoximine compared to the isomeric ratio in the filtrate, and (c) recrystallizing from a mixture of acid with pKa less than 2.0 and alcohol and non-polar solvent to produce crystals of pure L-buthionine-S-sulfoximine acid addition salt, (d) optionally converting said acid addition salt to L-buthionine-S-sulfoximine, i.e., the free zwitterion.

In still a further embodiment it has been discovered that the isomers of L-buthionine-SR-sulfoximine can be separated chromatographically by a method comprising the steps of:

(a) preparing an aqueous solution of L-buthionine-SR-sulfoximine, (b) applying said solution to a reverse-phase C-18 silica column previously equilibrated with D-proline and cupric salt, (c) eluting with D-proline and cupric salt and collecting fractions, (d) analyzing said fractions for isomer content, (e) combining fractions to obtain a pool containing substantially one isomer, (f) removing cupric salt and D-proline.

The term "pure" in "pure diastereomer", "pure L-buthionine-S-sulfoximine" and "pure L-buthionine-R-sulfoximine" means that at least 99% of the buthionine sulfoximine is one isomer which is the named isomer where one is named.

The term "enriched" means a greater ratio of named isomer than in the isomer mixture subjected to treatment to obtain enrichment.

DETAILED DESCRIPTION OF THE EMBODIMENT

L-buthionine-S-sulfoximine has the formula:

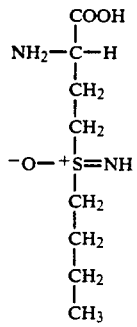

L-buthionine-R-sulfoximine has the formula:

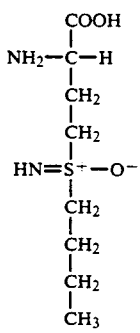

Acid addition salts of L-buthionine-S-sulfoximine and L-buthionine-R-sulfoximine are formed by conventional techniques involving reaction respectively of compounds of formulas (I) and (II) with mineral acids or organic carboxylic or sulfonic acids with pKa's less than 2.0. Pharmaceutically acceptable acid addition salts are derived, for example, from hydrochloric acid, sulfuric acid, phosphoric acid, maleic acid, methanesulfonic acid, and p-toluenesulfonic acid. Acid addition salts suitable for in vitro purposes but not for in vivo purposes are derived, for example, from trifluoroacetic acid, trichloroacetic acid and perchloric acid.

The aforementioned pure diastereoisomers can be administered alone or with a carrier either orally or parenterally, for example, at a dosage ranging from 0.1 to 30 mM/kg of animal body weight/day.

We turn now to the recrystallization method for preparing L-buthionine-S-sulfoximine from L-buthionine-SR-sulfoximine in more detail.

The concentration in step (a) preferably ranges from 0.6M to 1.0M, and very preferably is about 0.8M.

In steps (b) and (c), the acid is preferably a halogenated carboxylic acid. Very preferably said acid is trifluoroacetic acid. Another acid is trichloroacetic acid.

In steps (b) and (c), the alcohol is preferably a $C_1$ to $C_4$ alcohol. Suitable alcohols include, for example, methanol, n-propanol, l-propanol, n-butanol, s-butanol and t-butanol. Very preferably the alcohol is ethanol.

In steps (b) and (c), the non-polar solvent is preferably a $C_5$-$C_7$ hydrocarbon, for example, n-pentane, i-pentane, n-hexane, i-hexane, n-heptane or i-heptane or mixtures of these, e.g., petroleum ethers. A very preferred non-polar solvent is n-hexane.

Preferably, the filtrate of step (a) is dried to produce solid which is treated in step (b). Evaporation under vacuum is a preferred method of drying. In a preferred process, the resulting solid is first dissolved in ethanol, for example, from 10 to 15 ml/gm solid, very preferably 12.5 ml/gm solid, and then trifluoroacetic acid is added in an amount ranging from about 1.0 to about 1.5 ml per gram of solid and sufficient n-hexane (typically a volume equal to the volume of alcohol used) is added to cause formation of crystals. The trifluoroacetic acid is added in an amount in excess of stoichiometric and functions to form acid salt wherein the L-S-isomer is less soluble in mixtures of alcohol and non-polar solvent than the L-R-isomer, and the excess functions as a solvent.

The acid addition salt crystals resulting from step (c) are readily converted to crystals of L-buthionine-S-sulfoximine, i.e., the free zwitterion, for example, by neutralizing a concentrated aqueous solution, e.g., with NaOH, or by applying a solution to a column containing a strong acid ion exchange resin and separately eluting the acid and solution of L-buthionine-S-sulfoximine which can be dried to crystals thereof.

L-buthionine-R-sulfoximine is readily prepared from L-buthionine-SR-sulfoximine by repetitive recrystallization from water.

We turn now to the process where L-buthionine-SR-sulfoximine is separated into its isomers chromatographically.

Typically in step (a) concentrations range from 1 to 10 mM.

In step (b) the amount of solution applied to the column is 10 to 100 microliters for a column 0.46×25 cm. In steps (b) and (c) the equilibrating and eluting buffer typically is 17 mM D-proline and 8 mM cupric acetate. The flow rate for equilibrating in step (b) and for eluting in step (c) typically is 0.5 ml/min.

The fractions are readily analyzed by mixing samples therefrom with o-phthalaldehyde reagent (6.0 mM o-phthalaldehyde, 70 mM mercaptoethanol, 7.0 mM EDTA and 0.1% (w/v) Brig 35 in 0.4M sodium borate, pH 9.4-see Benson, J. R., et al, Proc. Natl. Acad. Sci, 72 619–622 (1975)), and determining the fluorescence of the resulting solution (excitation at 355 millimicrons and emission at 455 millimicrons). The data is plotted to identify the elution times for the L-S- and L-R-isomers. The first peak indicates the L-S-isomer and the next peak the L-R-isomer as shown by X-ray diffraction studies.

For step (f), copper is removed from pools from step (e) by passage through small columns of Chelex resin (a metal binding resin). For D-proline removal, the effluent from copper removal is applied to small columns of Dowex 50 (H+), a strong acid cation exchange resin, and D-proline and pure buthionine sulfoximine isomer are separately eluted with increasing concentrations of HCl.

The aforementioned method for recrystallizing to form pure L-S-isomer from L-buthionine-SR-sulfoximine has been found to have more general application, i.e., to be useful for obtaining L-S-isomer from L-(S-$C_3$–$C_6$-alkyl)homocysteine-SR-sulfoximines such as L-hexathionine-SR-sulfoximine and L-prothionine-SR-sulfoximine.

Thus in a broad embodiment, the instant invention is directed to a method of making pure L-(S-$C_3$–$C_6$-alkyl)-homocysteine-S-sulfoximines or acid addition salts thereon from L-(S-($C_3$–$C_6$-alkyl)homocysteine-SR-sulfoximines by the steps comprising:

(a) forming an aqueous solution of L-(S-$C_3$–$C_6$alkyl)-homocysteine-SR-sulfoximine in water in a concentration such that on cooling crystals enriched in L-(S-$C_3$–$C_6$-alkyl)homocysteine-R-sulfoximine form and cooling to form said crystals and a filtrate enriched in L-(S-$C_3$–$C_6$-alkyl)homocysteine-S-sulfoximine, and (b) treating the filtrate to produce a substantially water free solution of L-(S-$C_3$–$C_6$-alkyl)homocysteine-SR-sulfoximine enriched in the L-S-diastereomer compared to the isomeric ratio in said solution in step (a), in acid with a pKa less than 2.0 and alcohol and adding a non-polar solvent to produce crystals enriched in L-S-diastereomer compared to the isomeric ratio in said filtrate.

The resulting acid salt is readily converted to the free zwitterion by the methods of neutralization and absorbtion to and elution from strong acid cation exchange resin previously described.

The invention is illustrated by following examples:

EXAMPLE I

L-buthionine-SR-sulfoximine is prepared as described in Griffith, O. W., The Journal of Biological Chemistry, Vol. 257, No. 22, pp. 13704–13712, 1982. Such preparation is as follows: L-methionine, obtained commercially, is reductively demethylated using sodium in liquid ammonia to produce L-homocysteine. The L-homocysteine is alkylated with 1-bromobutane to form L-buthionine. The L-buthionine is converted to L-buthionine-SR-sulfoximine by reaction with sodium azide in chloroform/sulfuric acid. The L-buthionine-SR-sulfoximine product is isolated by chromatography on Dowex 50($H^+$) resin. L-buthionine-SR-sulfoximine. 6 gms, containing approximately equal amounts of the two diastereomers was dissolved in 34 ml of hot water (boiling water bath) to a final concentration of 0.8M. The solution was allowed to cool; crystallization occurred spontaneously. After standing overnight at 4° C., the crystals were collected by filtration. The filtrate was evaporated to dryness under reduced pressure. The solid (4.1 gms) was suspended in 50 ml of absolute ethanol, and 5 ml of trifluoroacetic acid was added dropwise. Hexane, 50 ml, was slowly added over a period of about 10 minutes to the stirred, clear solution. Stirring was then stopped, and crystallization was allowed to occur at room temperature. After 2 hours, the crystals were collected by filtration, washed with hexane and ether, and dried under vacuum. The yield was 2.8 gms. The crystals, 2.8 gms, are added to 35 ml of ethanol with stirring to form a solution. To this solution is added with stirring 3.5 ml of trifluoroacetic acid, followed by 35 ml of hexane (added slowly over a 10 minute period). Then stirring is stopped and crystallization is allowed to occur at room temperature. After 2 hours the crystals are collected by filtration, washed with hexane and ether, and dried under vacuum. The yield is 1.6 gms. The crystals consist of L-buthionine-S-sulfoximine trifluoroacetic acid addition salt (of greater than 99% purity). The yield is about 50% based on the initial L-buthionine-S-sulfoximine content of the starting material. The acid addition salt is converted to pure free zwitterion by dissolving in water, 20 ml, applying the resulting solution to a column of Dowex 50 ($H^+$), 1.5×20 cm, then washing with water to elute trifluoroacetic acid leaving L-buthionine-S-sulfoximine bound to the resin. The resin is washed with 1 liter of 3M ammonium hydroxide, and the eluent collected in 10 ml fractions. The fractions containing amino acid are pooled, evaporated to dryness at reduced pressure and traces of ammonia are removed by treating with water and evaporating.

EXAMPLE II

The crystals obtained from recrystallizing L-buthionine-SR-sulfoximine from water in Example I, 1.5 gms, are combined with similar preparations to assemble 10 gms of crystals. These are dissolved in 56 ml of hot water (boiling water bath). The solution is allowed to cool; crystallization occurs spontaneously. After standing overnight at 4° C., the crystals are collected by filtration (4.8 gms). Recrystallization two additional times from hot water gives 1.08 gms of 99.7% pure L-buthionine-R-sulfoximine. Recrystallization of that material 3 more times from hot water gives 0.13 gms of 99.99% pure L-buthionine-R-sulfoximine.

EXAMPLE III

L-buthionine-SR-sulfoximine (prepared as described in Griffith, O. W., The Journal of Biological Chemistry, Vol. 257, No. 22, pp. 13704–13712, 1982), 0.11 gms, containing approximately equal amounts of the two diastereomers is dissolved in 10 ml of room temperature water.

From the resulting solution 0.1 ml was injected onto a reverse-phase C-18 silica column (0.46×25 cm) equilibrated and eluted with 17 mM D-proline and 8 mM cupric acetate in water at a flow rate of 0.5 ml/min. Fractions of 0.25 ml were collected from 28 minutes to 35 minutes. The amino acid content of each fraction was determined. L-buthionine-S-sulfoximine eluted in a peak centered at 30.4 minutes and L-buthionine-R-sulfoximine eluted in a peak centered at 33.4 minutes. Appropriate fractions from up to 10 runs were pooled and passed through Chelex resin to remove copper. In each case, the proline was removed by applying the $Cu^{++}$-free effluent to small columns (0.5×7 cm) of Dowex 50 ($H^+$), a strong acid cation exchange resin in the hydrogen form. In each case, the resin was washed with three 2 ml portions of water and then with three 2 ml portions each of 0.5, 1.0, 1.5, 2.0, 3.0, and 4.0M HCl in succession; elution with 4M HCl was continued until no further buthionine sulfoximine eluted. Two ml fractions were collected. Proline elutes with 1.5M HCl; buthionine sulfoximine elutes with 4M HCl. The buthionine sulfoximine fractions were evaporated to dryness at reduced pressure, and the residues were dissolved in a small volume of water and stored at −20° C. In one case the product was substantially pure aqueous solution of L-buthionine-S-sulfoximine hydrochloride. In the other case the product was a substantially pure aqueous solution of L-buthionine-R-sulfoximine hydrochloride. Drying produces the crystalline salts.

EXAMPLE IV

L-buthionine-S-sulfoximine, L-buthionine-R-sulfoximine and D-buthionine-SR-sulfoximine were assayed for ability to inhibit gamma-glutamylcysteine synthetase.

The assay procedure used is similar to that described in Griffith, O. W., J. Biol. Chem. 257, 13704–13712 (1982).

The assay is based on the following reactions wherein GS is used to denote gamma-glutamylcysteine synthetase, PK is used to denote pyruvate kinase, LDH is used to denote lactate dehydrogenase, NADH is used to denote reduced beta-nicotinamide adenine dinucleotide, NAD+ is used to denote oxidized beta-nictoninamide adenine dinucleotide, ATP is used to denote adenosine triphosphate, ADP is used to denote adenosine diphosphate, and Pi is used to denote inorganic phosphate.

| Catalyst | Reaction |
| --- | --- |
| (1) GS | Glutamate + α-Aminobutyrate + ATP ⟶ gamma-Glutamylaminobutyrate + ADP + Pi |
| (2) PK | Phosphoenolpyruvate + ADP ⇌ Pyruvate + ATP |
| (3) LDH | Pyruvate + NADH ⇌ Lactate + NAD+ + H+ |

The assay is based on the fact that the velocity of the reaction to produce gamma-glutamylaminobutyrate is reduced to the extent that GS is inhibited. Alpha-aminobutyrate is used as a substitute for cysteine, the natural substrate, because it is more stable. Reactions (2) and (3) are a detection system for ADP wherein ADP, as it is produced, reacts with phosphoenolpyruvate to produce pyruate, which reacts with NADH to produce NAD+. The conversion of NADH to NAD+ is monitored in a spectrophotometer based on the fact that NADH absorbs light at 340 mμ and NAD+ does not. Thus, progress of the GS reaction results in a decrease in the absorbence of the solution at 340 mμ and, if GS is inhibited, the decrease in absorbence at 340 mμ occurs at a slower rate. Such studies are carried out at several concentrations of inhibitor. For reversible inhibitors, the results are readily compiled in a Lineweaver-Burk plot of the reciprocal of the reaction velocity versus the reciprocal of concentration of glutamate, and the data can be analyzed to provide Ki values wherein small Ki values indicate strong inhibitors. For irreversible inhibitors, the process of the GS reaction is not constant with time but instead decreases with time to eventually become zero.

Each test for inhibition was carried out in a cuvette containing in a final volume of 1 ml the following: 150 mM Tris-HCl buffer (pH 8.2), 75 mM KCl, 10 mM ATP, 5 mM phosphoenolpyruvate, 25 mM MgCl$_2$, 1 to 5 mM L-glutamate, 10 mM α-amino-L-butyrate, 0.3 mM NADH, 0.2 mM EDTA, 10 International Units of PK, 10 International Units of LDH and 0.03 International Units of GS. For each reversible inhibitor 16 sets of test runs were made. Four sets of runs were made with 1 mM glutamate; 4 sets of runs were made with 1.7 mM glutamate; 4 sets of runs was made with 2.5 mM glutamate and 4 sets of runs were made with 5 mM glutamate. At each glutamate concentration, one set of runs were made with no inhibitor. For studies with L-buthionine-R-sulfoximine the other 3 sets of runs contained 0.05, 0.1 or 0.2 mM inhibitor. For studies with D-buthionine-SR-sulfoximine, the other 3 sets of runs contained 2, 5 or 10 mM inhibitor.

For each test run the temperature was kept at 37° C. and GS was added last to start the reaction. The reaction velocity was followed from the decrease in absorbence at 340 mμ (a decrease of 0.62 in optical density indicates 0.1 μmol of product was formed).

A Lineweaver-Burk plot was then prepared. Data obtained in studies without inhibitor indicated that the Km for glutamate was 1.7±0.3 mM. Data obtained in studies with L-buthionine-R-sulfoximine indicated that it is a reversible inhibitor with a Ki of 0.11 mM and that its binding is competitive with glutamate. Data obtained in studies with D-buthionine-SR-sulfoximine indicated that it is a reversible inhibitor with a Ki of 5.2 mM and that its binding is competitive with glutamate.

Test runs for inhibition with L-buthionine-S-sulfoximine were made in reaction mixtures identical to those described for the reversible inhibitors except the concentration of L-buthionine-S-sulfoximine added was 0, 0.01 or 0.1 mM. In reaction mixtures containing L-buthionine-S-sulfoximine the rate of reaction decreased with time indicating irreversible inhibition. Complete inhibition was obtained in less than 5 min with either concentration tested. The inhibition could not be reversed by dilution of the reaction mixture or by gel permeation chromatography of the reaction mixture is buffers containing ATP and MgCl$_2$.

EXAMPLE V

L-buthionine-S-sulfoximine, L-buthionine-R-sulfoximine, L-buthionine-SR-sulfoximine and D-buthionine-SR-sulfoximine were assayed for ability to cause glutathione depletion in mice.

The procedure used is describe in Griffith, O. W., J. Biol. Chem. 257, 13704–13712 (1982). Tissue glutathione levels were determined as described in Griffith, O. W., Anal. Biochem. 106, 207–212, (1980).

These procedures except for the method of glutathione level determination are set forth in the following paragraph. The glutathione level determination procedure utilizes an enzymatic recycling assay in which glutathione disulfide is reduced to glutathione by glutathione reductase and glutathione is immediately reoxidized to glutathione disulfide by 5,5'-dithiobis(2-nitrobenzoic acid) with concomitant production of 2-nitro-3-mercaptobenzoic acid, a yellow chromophore with a strong absorbance at 412 millimicrons, the rate of production of which is monitored spectrophotometrically; the rate of these coupled reactions increases linearly with the amount of total glutathione (i.e., glutathione plus glutathione disulfide) present.

Thirty two mice were given physiological saline, 4 mice were given 0.4 mmole/kg of L-buthionine-SR-sulfoximine, 4 mice were given 0.2 mmole/kg of L-buthionine-S-sulfoximine, 4 mice were given 0.2 mmoles/kg of L-buthionine-R-sulfoximine and 4 mice were given 0.4 mmole/kg or D-buthionine-SR-sulfoximine. All injections were given intraperitoneally. Two hours after injection, the mice were killed, and the glutathione levels in the brain, liver, pancreas, and kidney were determined.

None of the compounds caused significant depletion of glutathione in brain. L-Buthionine-SR-sulfoximine and L-buthionine-S-sulfoximine caused the glutathione level of pancreas to be decreased to about 42% of control. L-Buthionine-SR-sulfoximine and L-buthionine-S-sulfoximine caused the glutathione level of liver to be decreased to 52% and 41% of control, respectively. L-buthionine-R-sulfoximine and D-buthionine-SR-sulfoximine did not cause significant depletion of glutathione in pancreas or liver. L-Buthionine-SR-sulfoximine, L-buthionine-S-sulfoximine, L-buthionine-R-sulfoximine, and D-buthionine-SR-sulfoximine caused glutathione level of kidney to be decreased to 27%, 27%, 87%, and 70% of control, respectively. In kidney the decrease in glutathione level observed in mice given L-buthionine-R-sulfoximine or D-buthionine-SR-sulfoximine is probably attributable to inhibition of L-glutamylcysteine uptake from the tubule as shown previously for L-buthionine sulfone by Anderson and Meister (Anderson, M. E., and Meister, A., Proc. Natl. Acad. Sci., Vol. 80, pp. 707–711, 1983).

EXAMPLE VI

The transport of L-buthionine-S-sulfoximine and L-buthionine-R-sulfoximine into tissues was examined using preparations of each isomer radiolabeled with $^{35}S$.

L-$[^{35}S]$-Buthionine-SR-sulfoximine was prepared from L-$[^{35}S]$methionine as described previously (Griffith, O. W., J. Biol. Chem. 257, 13704–13712 (1982)). The preparation was separated into L-$[^{35}S]$-buthionine-S-sulfoximine and L-$[^{35}S]$-buthionine-R-sulfoximine by chromatography using $Cu^{++}$ D-proline buffer as described in Example III.

Twelve mice were injected intraperitoneally with L-$[^{35}S]$-buthionine-S-sulfoximine and 12 mice were injected intraperitoneally with L-buthionine-R-sulfoximine. For all mice the dose was 2 mmole/kg. After 2 hours the mice were sacrificed, and the radioactivity contained in the various tissues was determined by liquid scintillation counting. From that determination and from the known specific activity of the compounds injected, the tissue content of either L-buthionine-S-sulfoximine or L-buthionine-R-sulfoximine was calculated. The results in $\mu$mole/gm tissue were as follows (tissue, content of L-buthionine-S-sulfoximine, content of L-buthionine-R-sulfoximine): brain, 0.11, 0.17; lung, 0.53, 0.55; heart, 0.33, 0.49; liver, 0.11, 0.16; spleen 0.51, 0.59; small intestine, 0.34, 0.39; large intestine, 0.25, 0.20; testes, 0.45, 0.50; skeletal muscle, 0.18, 0.24.

The results indicate that some tissues (e.g., heart and liver) take up, or retain, or both, L-buthionine-R-sulfoximine more effectively than L-buthionine-S-sulfoximine. The results therefore suggest that the addition of L-buthionine-R-sulfoximine to a therapeutic dose of L-buthionine-S-sulfoximine will decrease the uptake of L-buthionine-S-sulfoximine by heart and liver. Since decreased uptake of L-buthionine-S-sulfoximine is associated with smaller decreases in glutathione content, heart and liver would be partially protected from the adverse effects of glutathione depletion.

Variations in the invention will be obvious to those skilled in the art. Therefore the invention is defined by the claims.

What is claimed is:

1. Pure L-(S-$C_3$-$C_6$-alkyl)homocysteine-S-sulfoximines and acid addition salts thereof.

2. The compounds of claim 1 which are pure L-(S-$C_3$-$C_6$-alkyl)homocysteine-S-sulfoximines.

3. The compound of claim 2 which is L-buthionine-S-sulfoximine.

4. The compounds of claim 1 which are pure L-buthionine-S-sulfoximine and acid addition salts thereof.

5. Pure L-buthionine-R-sulfoximine and acid addition salts thereof.

* * * * *